United States Patent
Batley et al.

(10) Patent No.: US 12,213,533 B2
(45) Date of Patent: Feb. 4, 2025

(54) VAPORIZER DEVICES

(71) Applicant: JUUL Labs, Inc., San Francisco, CA (US)

(72) Inventors: Oliver J. Batley, Cambridge (GB); Joshua A. de Gromoboy Dabrowicki, Cambridge (GB); Alex M. Gee, Cambridge (GB); Zhenqiang Lin, Cambridge (GB); Christopher James Rosser, Cambridge (GB); James P. Westley, Cambridge (GB)

(73) Assignee: JUUL Labs, Inc., Washington, DC (US)

( * ) Notice: Subject to any disclaimer, the term of this patent is extended or adjusted under 35 U.S.C. 154(b) by 784 days.

(21) Appl. No.: 17/347,980

(22) Filed: Jun. 15, 2021

(65) Prior Publication Data
US 2021/0307402 A1 Oct. 7, 2021

Related U.S. Application Data

(63) Continuation of application No. PCT/US2020/013758, filed on Jan. 15, 2020.
(Continued)

(51) Int. Cl.
*A24F 40/51* (2020.01)
*A24F 40/60* (2020.01)

(52) U.S. Cl.
CPC ............. *A24F 40/51* (2020.01); *A24F 40/60* (2020.01)

(58) Field of Classification Search
CPC .................................. A24F 40/51; A24F 40/60
See application file for complete search history.

(56) References Cited

U.S. PATENT DOCUMENTS 2,867,706 A * 1/1959 Statham .................. G01L 27/00
73/514.12
2,935,710 A * 5/1960 Curtis .................. G01L 9/0083
338/41
(Continued)

FOREIGN PATENT DOCUMENTS

CA 2935072 C 5/2018
CN 100589726 C 2/2010
(Continued)

OTHER PUBLICATIONS

PCT/US2020/013758, Jan. 15, 2020, WO 2020/150400.
Goniewicz, et al (Jan. 31, 2013), "Nicotine Levels in Electronic Cigarettes", Nicotine & Tobacco Research, 15(1):158-166.

*Primary Examiner* — Russell E Sparks
(74) *Attorney, Agent, or Firm* — Mintz, Levin, Cohn, Ferris, Glovsky and Popeo, P.C.

(57) ABSTRACT

Vaporizer devices are disclosed. In one exemplary embodiment, a vaporizer device can include a vaporizer body including a first airflow path extending at least partially therethrough, and a sensor assembly residing at least partially within the vaporizer body. The sensor assembly includes a flexible sensor that is in communication with the first airflow path. The flexible sensor is configured to reversibly deflect from an initial state to a first state in response to a first user-activated force representing air being drawn through the first airflow path, and configured to reversibly deflect from the initial state to a second state in response to a second user-activated force representing an acceleration of the vaporizer body. Sensor assemblies for a vaporizer device are also provided.

20 Claims, 7 Drawing Sheets

Related U.S. Application Data

(60) Provisional application No. 62/792,659, filed on Jan. 15, 2019.

(56) References Cited

U.S. PATENT DOCUMENTS

| | | |
|---|---|---|
| 4,810,854 A | 3/1989 | Jursich et al. |
| 4,947,874 A | 8/1990 | Brooks et al. |
| 4,947,875 A | 8/1990 | Brooks et al. |
| 5,649,554 A | 7/1997 | Sprinkel et al. |
| 5,666,978 A | 9/1997 | Counts et al. |
| 6,513,524 B1 | 2/2003 | Storz |
| 6,516,796 B1 | 2/2003 | Cox et al. |
| 8,910,639 B2 | 12/2014 | Chang et al. |
| 9,004,073 B2 | 4/2015 | Tucker et al. |
| 9,072,321 B2 | 7/2015 | Liu |
| 9,282,772 B2 | 3/2016 | Tucker et al. |
| 9,326,547 B2 | 5/2016 | Tucker et al. |
| 9,326,550 B2 | 5/2016 | Hon |
| 9,339,062 B2 | 5/2016 | Hon |
| 9,427,026 B2 | 8/2016 | Wu |
| 9,474,306 B2 | 10/2016 | Tucker et al. |
| 9,668,523 B2 | 6/2017 | Tucker et al. |
| 9,687,027 B2 | 6/2017 | Poston et al. |
| 9,723,876 B2 | 8/2017 | Cadieux et al. |
| 9,770,055 B2 | 9/2017 | Cameron et al. |
| 9,772,216 B2 | 9/2017 | Poole et al. |
| 9,820,508 B2 | 11/2017 | Schmiesing et al. |
| 9,854,839 B2 | 1/2018 | Tucker et al. |
| 9,974,338 B2 | 5/2018 | Alarcon et al. |
| 9,986,762 B2 | 6/2018 | Alarcon et al. |
| 10,004,259 B2 | 6/2018 | Sebastian et al. |
| 10,058,122 B2 | 8/2018 | Steingraber et al. |
| 10,058,128 B2 | 8/2018 | Cameron et al. |
| 10,085,486 B2 | 10/2018 | Cameron |
| 10,090,693 B2 | 10/2018 | Alarcon |
| 10,111,467 B1 | 10/2018 | Arnel et al. |
| 10,130,123 B2 | 11/2018 | Hatton et al. |
| 10,143,233 B2 | 12/2018 | Dubief et al. |
| 10,188,148 B2 | 1/2019 | Althorpe et al. |
| 10,194,693 B2 | 2/2019 | Wensley et al. |
| 10,276,898 B2 | 4/2019 | Leadley |
| 10,292,435 B2 | 5/2019 | Qiu |
| 10,327,478 B2 | 6/2019 | Hon |
| 10,342,264 B2 | 7/2019 | Hon |
| 10,357,060 B2 | 7/2019 | Rostami et al. |
| 10,383,367 B2 | 8/2019 | Rasmussen et al. |
| 10,405,583 B2 | 9/2019 | Tucker et al. |
| 10,420,374 B2 | 9/2019 | Liu |
| 10,517,331 B2 | 12/2019 | Atkins et al. |
| 2005/0268911 A1 | 12/2005 | Cross et al. |
| 2008/0105257 A1 | 5/2008 | Klasek et al. |
| 2013/0255702 A1 | 10/2013 | Griffith et al. |
| 2014/0096781 A1 | 4/2014 | Sears et al. |
| 2014/0096782 A1 | 4/2014 | Ampolini et al. |
| 2014/0150785 A1 | 6/2014 | Malik et al. |
| 2014/0261486 A1 | 9/2014 | Potter et al. |
| 2014/0276536 A1 | 9/2014 | Estes |
| 2014/0355969 A1 | 12/2014 | Stern |
| 2014/0360516 A1 | 12/2014 | Liu |
| 2015/0114409 A1 | 4/2015 | Brammer et al. |
| 2015/0282527 A1* | 10/2015 | Henry, Jr. ............... G01F 1/28 |
| | | 131/328 |
| 2015/0289567 A1 | 10/2015 | Liu |
| 2015/0313284 A1 | 11/2015 | Liu |
| 2015/0351455 A1 | 12/2015 | Liu |
| 2016/0044965 A1 | 2/2016 | Liu |
| 2016/0088874 A1 | 3/2016 | Lipowicz |
| 2016/0206002 A1 | 7/2016 | Borkovec et al. |
| 2016/0249684 A1 | 9/2016 | Liu |
| 2016/0262453 A1 | 9/2016 | Ampolini et al. |
| 2016/0309785 A1 | 10/2016 | Holtz |
| 2016/0309786 A1 | 10/2016 | Holtz et al. |
| 2016/0331030 A1 | 11/2016 | Ampolini et al. |
| 2016/0331913 A1 | 11/2016 | Bourque |
| 2016/0356751 A1 | 12/2016 | Blackley |
| 2016/0360784 A1 | 12/2016 | Liu |
| 2016/0363570 A1 | 12/2016 | Blackley |
| 2016/0363917 A1 | 12/2016 | Blackley |
| 2016/0366725 A1 | 12/2016 | Tucker et al. |
| 2016/0366940 A1 | 12/2016 | Liu |
| 2016/0367925 A1 | 12/2016 | Blackley |
| 2016/0370335 A1 | 12/2016 | Blackley |
| 2017/0006917 A1 | 1/2017 | Alvarez |
| 2017/0006919 A1 | 1/2017 | Liu |
| 2017/0018000 A1 | 1/2017 | Cameron |
| 2017/0020188 A1 | 1/2017 | Cameron |
| 2017/0020195 A1 | 1/2017 | Cameron |
| 2017/0020196 A1 | 1/2017 | Cameron |
| 2017/0020197 A1 | 1/2017 | Cameron |
| 2017/0027229 A1 | 2/2017 | Cameron |
| 2017/0042225 A1 | 2/2017 | Liu |
| 2017/0042230 A1 | 2/2017 | Cameron |
| 2017/0042231 A1 | 2/2017 | Cameron |
| 2017/0046357 A1 | 2/2017 | Cameron |
| 2017/0046738 A1 | 2/2017 | Cameron |
| 2017/0055588 A1 | 3/2017 | Cameron |
| 2017/0086496 A1 | 3/2017 | Cameron |
| 2017/0086497 A1 | 3/2017 | Cameron |
| 2017/0086503 A1 | 3/2017 | Cameron |
| 2017/0086504 A1 | 3/2017 | Cameron |
| 2017/0091853 A1 | 3/2017 | Cameron |
| 2017/0092106 A1 | 3/2017 | Cameron |
| 2017/0093960 A1 | 3/2017 | Cameron |
| 2017/0093981 A1 | 3/2017 | Cameron |
| 2017/0119052 A1 | 5/2017 | Williams et al. |
| 2017/0119058 A1 | 5/2017 | Cameron |
| 2017/0135401 A1 | 5/2017 | Dickens |
| 2017/0135407 A1 | 5/2017 | Cameron |
| 2017/0135408 A1 | 5/2017 | Cameron |
| 2017/0135409 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136196 A1 | 5/2017 | Davidson et al. |
| 2017/0136301 A1 | 5/2017 | Cameron |
| 2017/0143038 A1 | 5/2017 | Dickens |
| 2017/0197046 A1 | 7/2017 | Buchberger |
| 2017/0208866 A1 | 7/2017 | Liu |
| 2017/0214261 A1 | 7/2017 | Gratton |
| 2017/0215476 A1 | 8/2017 | Dickens et al. |
| 2017/0224014 A1 | 8/2017 | Fraser |
| 2017/0231284 A1 | 8/2017 | Newns et al. |
| 2017/0251718 A1 | 9/2017 | Armoush et al. |
| 2017/0251725 A1 | 9/2017 | Buchberger et al. |
| 2017/0258138 A1 | 9/2017 | Rostami et al. |
| 2017/0258140 A1 | 9/2017 | Rostami et al. |
| 2017/0301898 A1 | 10/2017 | Lin et al. |
| 2017/0325289 A1 | 11/2017 | Liu |
| 2017/0325504 A1 | 11/2017 | Liu et al. |
| 2017/0367402 A1 | 12/2017 | Lau et al. |
| 2017/0367407 A1 | 12/2017 | Althorpe et al. |
| 2018/0007741 A1 | 1/2018 | Metz et al. |
| 2018/0020728 A1 | 1/2018 | Alarcon et al. |
| 2018/0027877 A1 | 2/2018 | Tucker et al. |
| 2018/0042306 A1 | 2/2018 | Atkins et al. |
| 2018/0043114 A1 | 2/2018 | Bowen et al. |
| 2018/0064169 A1 | 3/2018 | Biel et al. |
| 2018/0077967 A1 | 3/2018 | Hatton et al. |
| 2018/0103685 A1 | 4/2018 | Yener |
| 2018/0146715 A1 | 5/2018 | Takeuchi et al. |
| 2018/0160735 A1 | 6/2018 | Borkovec et al. |
| 2018/0184711 A1* | 7/2018 | Dickens ............... A24F 40/51 |
| 2018/0199627 A1 | 7/2018 | Bowen et al. |
| 2018/0220707 A1 | 8/2018 | Biel et al. |
| 2018/0279682 A1 | 10/2018 | Guo et al. |
| 2018/0296777 A1 | 10/2018 | Terry et al. |
| 2018/0303169 A1 | 10/2018 | Sears et al. |
| 2018/0333547 A1* | 11/2018 | Freeman ............... A24F 40/485 |
| 2019/0104767 A1 | 4/2019 | Hatton et al. |
| 2019/0159519 A1 | 5/2019 | Bowen et al. |
| 2019/0166913 A1 | 6/2019 | Trzecieski |
| 2020/0000146 A1 | 1/2020 | Anderson et al. |

(56) References Cited

U.S. PATENT DOCUMENTS

| | | |
|---|---|---|
| 2020/0113245 A1 | 4/2020 | Rosser et al. |
| 2020/0114094 A1 | 4/2020 | Atkins et al. |
| 2020/0127475 A1 | 4/2020 | Cheung et al. |
| 2020/0128874 A1 | 4/2020 | Atkins et al. |
| 2020/0130911 A1 | 4/2020 | Bhalla et al. |

FOREIGN PATENT DOCUMENTS

| | | | |
|---|---|---|---|
| CN | 101557728 B | 4/2011 | |
| CN | 103221084 A | 7/2013 | |
| CN | 102655773 B | 5/2016 | |
| CN | 104055223 B | 10/2017 | |
| CN | 107708452 A | 2/2018 | |
| EP | 0358114 A2 | 3/1990 | |
| GB | 2566857 B | 8/2019 | |
| JP | 2005034021 A | 2/2005 | |
| JP | 2015504653 A | 2/2015 | |
| KR | 101682319 B1 | 12/2016 | |
| KR | 101924068 B1 | 11/2018 | |
| KR | 102017873 B1 | 9/2019 | |
| TW | 201808127 A | 3/2018 | |
| WO | WO-2007146893 A2 * | 12/2007 | ............... G01F 1/28 |
| WO | WO-2011033396 A2 * | 3/2011 | ........... A24F 40/485 |
| WO | WO 2012134117 A2 | 10/2012 | |
| WO | WO 2013020220 A1 | 2/2013 | |
| WO | WO 2014068504 A2 | 5/2014 | |
| WO | WO 2014144678 A2 | 9/2014 | |
| WO | WO 2015003327 A1 | 1/2015 | |
| WO | WO 2015006929 A1 | 1/2015 | |
| WO | WO 2015077998 A1 | 6/2015 | |
| WO | WO 2015120588 A1 | 8/2015 | |
| WO | WO 2015123831 A1 | 8/2015 | |
| WO | WO 2015149368 A1 | 10/2015 | |
| WO | WO 2015157893 A1 | 10/2015 | |
| WO | WO 2015168912 A1 | 11/2015 | |
| WO | WO 2015180027 A1 | 12/2015 | |
| WO | WO 2015180061 A1 | 12/2015 | |
| WO | WO 2015180062 A1 | 12/2015 | |
| WO | WO 2015192326 A1 | 12/2015 | |
| WO | WO-2016009202 A1 * | 1/2016 | ............. A24F 15/18 |
| WO | WO 2016049855 A1 | 4/2016 | |
| WO | WO 2016065532 A1 | 5/2016 | |
| WO | WO 2016065606 A1 | 5/2016 | |
| WO | WO 2016074228 A1 | 5/2016 | |
| WO | WO 2016074229 A1 | 5/2016 | |
| WO | WO 2016074237 A1 | 5/2016 | |
| WO | WO 2016079151 A1 | 5/2016 | |
| WO | WO 2016082217 A1 | 6/2016 | |
| WO | WO 2016090601 A1 | 6/2016 | |
| WO | WO 2016090602 A1 | 6/2016 | |
| WO | WO 2016108694 A1 | 7/2016 | |
| WO | WO 2016118005 A1 | 7/2016 | |
| WO | WO 2016119099 A1 | 8/2016 | |
| WO | WO 2016127401 A1 | 8/2016 | |
| WO | WO 2016128562 A1 | 8/2016 | |
| WO | WO 2016131755 A1 | 8/2016 | |
| WO | WO 2016138689 A1 | 9/2016 | |
| WO | WO 2016150019 A1 | 9/2016 | |
| WO | WO 2016166456 A1 | 10/2016 | |
| WO | WO 2016198879 A1 | 12/2016 | |
| WO | WO-2017001817 A1 | 1/2017 | |
| WO | WO 2017001818 A1 | 1/2017 | |
| WO | WO 2017001819 A1 | 1/2017 | |
| WO | WO 2017033007 A1 | 3/2017 | |
| WO | WO 2017055793 A1 | 4/2017 | |
| WO | WO 2017055866 A1 | 4/2017 | |
| WO | WO 2017064324 A1 | 4/2017 | |
| WO | WO 2017072239 A1 | 5/2017 | |
| WO | WO 2017082728 A1 | 5/2017 | |
| WO | WO 2017137554 A1 | 8/2017 | |
| WO | WO 2019173923 A1 | 9/2019 | |
| WO | WO 2019232086 A1 | 12/2019 | |
| WO | WO 2020006305 A1 | 1/2020 | |
| WO | WO 2020023547 A1 | 1/2020 | |
| WO | WO 2020091827 A1 | 5/2020 | |

* cited by examiner

VAPORIZER DEVICES

CROSS-REFERENCE TO RELATED APPLICATIONS

This application is a continuation application, filed under 35 U.S.C. § 120, of PCT International Patent Application No. PCT/US20/13758 with an International Filing Date of Jan. 15, 2020, and entitled "Vaporizer Devices," which claims priority to U.S. Provisional Patent Application No. 62/792,659 filed on Jan. 15, 2019, and entitled "Vaporizer Devices," the disclosures of all of which are incorporated herein by reference in their entirety.

TECHNICAL FIELD

The subject matter described herein relates to vaporizer devices, including a flexible sensor that is configured to detect a puff or a tap on the device.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a vaporizer cartridge (for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporizer device.

In some implementations, the vaporizable material can be drawn out of a reservoir and into the vaporization chamber via a wicking element (e.g., a wick). Drawing of the vaporizable material into the vaporization chamber can be at least partially due to capillary action provided by the wick as the wick pulls the vaporizable material along the wick in the direction of the vaporization chamber.

The heating element can be activated once airflow consistent with a user puffing on or drawing air through an outlet of the vaporizer device (e.g., an outlet of a vaporizer cartridge or of a mouthpiece of the device) is detected, typically by a pressure sensor. The pressure sensor is generally an analog pressure sensor that is surface mounted onto a rigid printed circuit board within the device. However, the longevity and sensing accuracy of these pressure sensors can be compromised. This is because such pressure sensors are typically designed to function in a fairly clean and dry environment, however, the environment within or around a vaporizer device can become dirty and/or moist throughout device use. As a result, such pressure sensors may come into contact with fluids (e.g., water and/or the vaporizable material), particulates, heat, and/or other complicating environmental factors whenever it is in use. To mitigate contact, and thus increase longevity, these pressure sensors typically include a small orifice. The small orifice, however, can become clogged with viscous material (e.g., condensate), thereby causing the sensors to fail.

Further, in some embodiments, vaporizer devices can also include a motion sensor, typically an accelerometer. The accelerometer is generally surface mounted onto a rigid printed circuit board of the device. The implementation of the accelerometer provides a sensing mechanism to detect tapping on the vaporizer device. Tap detection can be used for a variety of mechanisms. For example, tap detection can prompt a visual indication of the real-time battery charge of the device. Alternatively, or in addition, tap detection can be used to toggle between different modes of the device, such as a normal mode and an entertainment mode, and/or to lock and unlock the device. However, the incorporation of the accelerometer, particularly in conjunction with a pressure sensor, can lead to an increase in device manufacturing costs.

Accordingly, vaporizer devices that address one or more of these issues are desired.

SUMMARY

Aspects of the current subject matter relate to vaporizer devices and sensor assemblies for use in the vaporizer devices that include a dual function sensor that is configured to detect both puffing and tapping activity on the device by a user.

Vaporizer devices are disclosed. In one exemplary embodiment, a vaporizer device includes a vaporizer body including a first airflow path at least partially extending therethrough, and a sensor assembly residing at least partially within the vaporizer body. The sensor assembly includes a flexible sensor that is in communication with the first airflow path. The flexible sensor is configured to reversibly deflect from an initial state to a first state in response to a first user-activated force representing air being drawn through the first airflow path, and configured to reversibly deflect from the initial state to a second state in response to a second user-activated force representing an acceleration of the vaporizer body. In one embodiment, the acceleration can occur in response to a user tapping the vaporizer body.

In some embodiments, the flexible sensor can at least partially reside within the first airflow path. In other embodiments, the vaporizer body can include at least one inlet that can be configured to allow a portion of ambient air outside of the vaporizer body to pass into the vaporizer body and travel along the first airflow path.

In some embodiments, the sensor assembly can include a substrate residing within the vaporizer body in which a first end of the flexible sensor is coupled to the substrate and a second, opposing end of the flexible sensor is positioned in the first airflow path. In one embodiment, the substrate can include a printed circuit board assembly. In another embodiment, the substrate can be coupled to a printed circuit board assembly that at least partially resides within the vaporizer body.

In some embodiments, the sensor assembly can include a first substrate and a second substrate that each reside within the vaporizer body. A first end of the flexible sensor can be coupled to the first substrate and a second, opposing end of the flexible sensor can be coupled to the second substrate such that the flexible sensor defines a portion of the first airflow path.

In some embodiments, the flexible sensor can be configured to at least partially deflect at a first rate of deflection while the first user-activated force is being applied. In such embodiments, the flexible sensor can be configured to at least partially deflect at a second rate of deflection while the second-user activated force is being applied.

In some embodiments, the flexible sensor can deflect at a first frequency while the flexible sensor is in the first state and at a second frequency that is different than the first frequency while the flexible sensor is in the second state.

The flexible sensor can have a variety of configurations. For example, in some embodiments, the flexible sensor in the initial state can be straight. In other embodiments, the flexible sensor in the initial state can be curved. In yet other embodiments, the flexible can be configured as a cantilever.

In some embodiments, the flexible sensor can include a strain gauge. In another embodiment, the flexible sensor can be formed of at least one conductive polymer. In yet another embodiment, the flexible sensor can be formed of at least one piezoelectric material.

In some embodiments, the vaporizer device can include a weight element. The weight element can be coupled to an end of the flexible sensor that resides within a portion of the first airflow path.

In some embodiments, the vaporizer device can include a controller. The controller can be configured to receive a deflection signal in response to deflection of the flexible sensor, maintain a first user-activated force threshold and a second user-activated force threshold, compare the deflection signal to the first and second user-activated force thresholds, output a first signal when the deflection signal is less than the first user-activated force threshold, and output a second signal when the deflection signal is greater than the second user-activated force threshold. In one embodiment, the deflection of the flexible sensor can be from the initial state to the first state. In another embodiment, the deflection of the flexible sensor can be from the initial state to the second state.

In some embodiments, the vaporizer device can include a heating element. The output of the first signal can be operable to cause an activation of the heating element to vaporize at least a portion of vaporizable material within a reservoir of the vaporizer device. In other embodiments, the vaporizer device can include a light source, and the vaporizer body can include a power source. The output of the second signal can be operable to cause activation of the light source representing a power condition of the power source.

In some embodiments, the vaporizer device can include a cartridge that is selectively coupled to and removable from the vaporizer body. The cartridge can include a second airflow path that extends therethrough and a reservoir chamber that is configured to hold a vaporizable material. The second airflow path can be in fluid communication with the first airflow path.

Sensor assemblies for a vaporizer device are also disclosed. In one exemplary embodiment, a sensor assembly includes at least one substrate and a flexible sensor having at least one end coupled to the at least one substrate. The flexible sensor is configured to reversibly deflect from an initial state to a first state in response to a first user-activated force representing air being drawn through an airflow path of a vaporizer device, and configured to reversibly deflect from the initial state to a second state in response to a second user-activated force representing acceleration of the vaporizer device. In one embodiment, the acceleration can occur in response to a user tapping the vaporizer device.

The at least one substrate can have a variety of configurations. In one embodiment, the substrate can include a printed circuit board assembly that resides within the vaporizer device. In another embodiment, the at least one substrate can be coupled to a printed circuit board assembly that resides within the vaporizer device.

The flexible sensor can have a variety of configurations. For example, in some embodiments, the flexible sensor in the initial state can be straight. In other embodiments, the flexible sensor in the initial state can be curved. In yet other embodiments, the flexible can be configured as a cantilever.

In some embodiments, the flexible sensor can include a strain gauge. In another embodiment, the flexible sensor can be formed of at least one conductive polymer. In yet another embodiment, the flexible sensor can be formed of at least one piezoelectric material.

In some embodiments, the sensor assembly can include a controller. The controller can be configured to receive a deflection signal in response to deflection of the flexible sensor, maintain a first user-activated force threshold and a second user-activated force threshold, compare the deflection signal to the first and second user-activated force thresholds, output a first signal when the deflection signal is less than the first user-activated force threshold, and output a second signal when the deflection signal is greater than the second user-activated force threshold. In one embodiment, the deflection of the flexible sensor can be from the initial state to the first state. In another embodiment, the deflection of the flexible sensor can be from the initial state to the second state.

In some embodiments, the output of the first signal can be operable to cause activation of a heating element for vaporization of at least a portion of vaporizable material within a reservoir of the vaporizer device. In other embodiments, the output of the second signal can be operable to cause activation of a light source representing a power condition of a power source of the vaporizer device.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
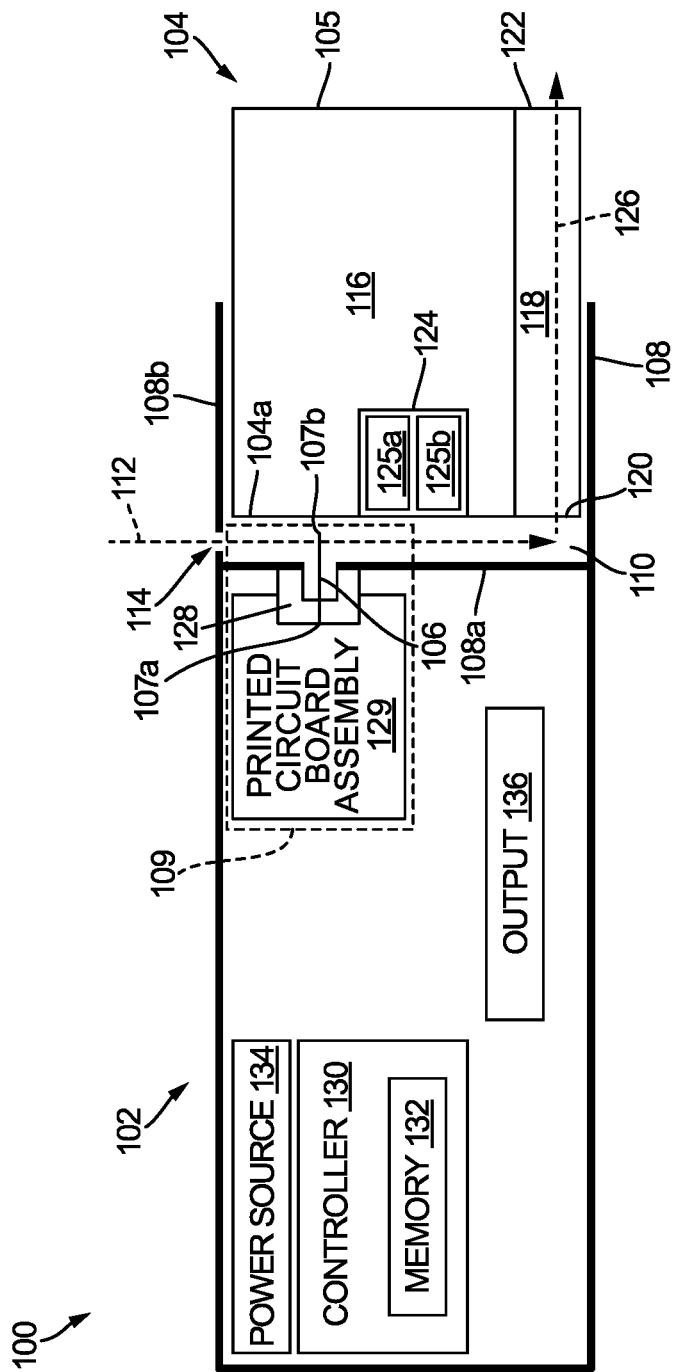
FIG. 1 is a partially transparent top view of a vaporizer device that includes a first embodiment of a flexible sensor.

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a vaporizer cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a vaporizer cartridge (for example, a part of the vaporizer device that contains the vaporizable material in a reservoir or other container) which can be refillable when empty, or disposable such that a new vaporizer cartridge containing additional vaporizable material of a same or different type can be used). A vaporizer device can be a cartridge-using vaporizer device, a cartridge-less vaporizer device, or a multi-use vaporizer device capable of use with or without a vaporizer cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material. For example, the liquid vaporizable material may include a carrier solution in which an active and/or inactive ingredient(s) are suspended or held in solution. Alternatively, the liquid vaporizable material may be a liquid form of the vaporizable material itself. The liquid vaporizable material can be capable of being completely vaporized. Alternatively, at least a portion of the liquid vaporizable material can remain after all of the material suitable for inhalation has been vaporized.

As mentioned above, existing vaporizer devices include a pressure sensor and an accelerometer that are configured to detect puffing and tapping on the device, respectfully. However, the need to include two separate elements for detecting puffing and tapping activity can lead to increased manufacturing costs of the vaporizer devices. Further, in order to detect a user's puff on the device, a pressure sensor is generally positioned within the vaporizer body and exposed to an airflow path delivering air to a vaporization chamber of the vaporizer device. It is common for vaporizer devices to employ an analog pressure sensor that includes a capacitive membrane, such as a capacitive membrane similar to those used in microphones. However, a capacitive membrane or a similar analog pressure sensor may be susceptible to malfunctions when contaminated with liquids that may be present within the airflow path including, for example, liquid vaporizable material, water, and/or the like. For example, being in contact with a liquid can dramatically change the capacitive properties of the capacitive membrane, thereby causing it to fail to perform as designed and preventing proper detection of a puff. Various features and devices are described below that improve upon or overcome these foregoing issues.

The vaporizer devices described herein utilize a flexible sensor that is configured to reversibly deflect in response to either a user puffing or tapping on the device. That is, a single sensor resides within the vaporizer device that can function as both a puff detector and a tap detector. As a result, this eliminates the need to include two different elements (e.g., a pressure sensor and accelerometer) to detect puffing and tapping activity. Further, the detection mechanism is associated with the mechanical properties of the flexible sensor. As such, the mechanical properties of the flexible sensor can be tailored for different devices and/or airflow paths of a device to effect a more accurate response during puffing and/or tapping on respective devices. Further, compared to capacitive sensors, the flexible sensors described herein are more robust, particularly when exposed to adverse environmental conditions. This is at least because during use of a vaporizer device, the mechanical response(s) of the flexible sensor (e.g., rate of deflection, frequency of deflection, and the like) are used to trigger detection of a puff or tap on the device.

A puffing activity can be associated with a user puffing on an outlet of the vaporizer device. For example, in some embodiments, the outlet of the device can be an outlet of a vaporizer cartridge coupled to a vaporizer body of the vaporizer device, whereas in other embodiments, the outlet is a mouthpiece coupled to an end of the vaporizer cartridge or of the vaporizer body. A tapping activity can be associated with a user tapping on the vaporizer device. For example, in some embodiments, the user can tap on a vaporizer body of the vaporizer device, on a vaporizer cartridge selectively coupled to and removable from the vaporizer body, or both.

The present vaporizer devices generally include a vaporizer body and a sensor assembly that resides at least partially within the vaporizer body. The sensor assembly includes a flexible sensor that is in communication with a first airflow path that at least partially extends through the vaporizer body. In some embodiments, at least a portion of the flexible sensor resides within the first airflow path, whereas in other embodiments, the flexible sensor can define a portion of the first airflow path.

The flexible sensor is configured to reversibly deflect from an initial state (e.g., when the vaporizer device is in a resting or standby mode) to a first state in response to a first user-activated force representing air being drawn through the first airflow path. As a result, when a user puffs on the device (e.g., on an end of a vaporizer cartridge coupled to the vaporizer body, or a mouthpiece coupled to the vaporizer cartridge), the air being drawn through the first airflow path can cause the flexible sensor to deflect. The flexible sensor is also configured to reversibly deflect from the initial state to a second state in response to a second user-activated force representing an acceleration of the vaporizer body. As a result, when a user taps on the vaporizer device (e.g., on the vaporizer body, on a vaporizer cartridge coupled to the vaporizer body, or both), the resulting motion of the device can cause the flexible sensor to deflect. As noted above, deflection of the flexible sensor can be used to trigger detection a puff or tap on the device by a user. A deflection of the flexible sensor can include stretching, bending, and/or vibrating of the flexible sensor, or any other possible movement of the flexible sensor to effect a deflection signal.

In some embodiments, the flexible sensor can be straight when in the initial state. In certain embodiments, the flexible sensor can be mechanically amplified. For example, in one embodiment, a weight element can be coupled to an end of the flexible that resides within a portion of the first airflow path. Mechanical amplification can help enable the detection of small amplitude taps on the device, which may otherwise go undetected due to the deflection of the flexible sensor being imperceptibly minimal.

In other embodiments, the flexible sensor can be mechanically dampened. For example, in one embodiment, the flexible sensor can be curved, and thus preloaded, when in the initial state. Mechanical dampening can help prevent false positives in detecting puffing and tapping activity. For example, the flexible sensor may be mechanically dampened to avoid the vaporizer device from being activated by de minimis deflections of the flexible sensor that do not correspond to actual puffing or tapping activity.

The flexible sensor can have a variety of configuration. In some embodiments, the flexible sensor is in the form of a beam. In one embodiment, the beam can have a first end fixedly attached to the vaporizer body and a second end (e.g., a free end), can be located within the first airflow path. In such embodiments, the beam can function similar to a cantilever in which the free end can move within the first airflow path to cause the flexible sensor to reversibly deflection in response to a puffing or tapping activity on the device. As described in more detail below, this deflection of the beam can be used as puff and tap detection mechanisms for the device.

In other embodiments, the first and second ends of the beam can be fixedly attached to the vaporizer body so as to define a portion of the first airflow path. In this way, for example, the beam can function similar to an elastic diaphragm in response to a puffing activity (e.g., expand outward in response to a pressure increase as air flows through the first airflow pathway). Further, the beam can also vibrate along at least a portion of its length in response to a tapping activity. As described in more detail below, these types of deflection of can be used as puff and tap detection mechanisms for the device.

In other embodiments, the beam can be reside completely within the first airflow path. As such, airflow passing through the first airflow path, and thus across the flexible sensor, causes the flexible sensor to vibrate. This effect is known as aerodynamic flutter, which occurs as a result of interactions between aerodynamics, stiffness of the flexible sensor, and inertial forces.

In some embodiments, the flexible sensor can be a strain gauge. For example, the strain gauge can include a metallic trace coupled to an insulating flexible substrate, away from a principle axis. As such, in use, the strain gauge can be stretched causing the trace to become narrower and longer. As a result, the electrical resistance increases, which can be measured using an electrical circuit (e.g., a Wheatstone bridge, and the like). In other embodiments, the flexible sensor can be formed of at least one conductive polymer. For example, a surface of the flexible sensor can be printed with a polymer containing conductive particles that are configured to move apart when the flexible sensor deflects (e.g., bends in one direction). The movement of the conductive particles causes an increase in electrical resistance. This increase in electrical resistance can be measured using a voltage divider. In yet other embodiments, the flexible sensor can be formed of at least one piezoelectric material.

In some embodiments, the sensor assembly can include at least one substrate residing within the vaporizer body in which a first end of the flexible sensor is coupled to the first substrate and a second, opposing end of the flexible sensor is positioned in the first airflow path. In other embodiments, a first end of the flexible sensor can be coupled to a first substrate of the at least one substrate and a second, opposing end of the flexible sensor can be coupled to a second substrate of the at least one substrate such that the flexible sensor defines a portion of the first airflow path. In one embodiment, the at least one substrate can include and/or be coupled with a printed circuit board assembly (PCBA) that at least partially resides within the vaporizer body. The printed circuit board assembly (PCBA) may include circuitry configured to detect a deflection of the flexible sensor. Furthermore, the printed circuit board assembly (PCBA) may include circuitry configured to respond to the deflection of the flexible sensor by generating a corresponding deflection signal.

In some embodiments, the flexible sensor can be configured to at least partially deflect at a first rate of deflection while the first user-activated force is being applied. Additionally, the flexible sensor can also be configured to at least partially deflect at a second rate of deflection while the second-user activated force is being applied. As such, the flexible sensor can deflect at a first frequency while the flexible sensor is in the first state and at a second frequency that is different than the first frequency while the flexible sensor is in the second state. Thus, the first and second rates of deflection and/or the resulting frequencies can be used to differentiate between a puffing activity and a tapping activity.

The vaporizer device can also include a power source (for example, a battery, which can be a rechargeable battery), and a controller (for example, a processor, circuitry, etc. capable of executing logic) for controlling delivery of heat from the heating element to cause a vaporizable material to be converted from a condensed form (for example, a solid-phase material, such as wax or the like, a liquid, a solution, a suspension, etc.) to the gas phase. The controller can be part of one or more printed circuit boards (PCBs) consistent with certain implementations of the current subject matter.

As noted, the printed circuit board assembly (PCBA) may include circuitry configured to generate, upon detecting a deflection of the flexible sensor, a corresponding deflection signal. In some implementations, the circuitry included in the printed circuit board assembly may be further configured to send, to the controller (e.g., a processor, circuitry, etc. capable of executing logic), the deflection signal for analysis by the controller to determine whether a puff or tap on the device has occurred. For example, the controller can be configured to receive a deflection signal in response to deflection of the flexible sensor, maintain a first user-activated force threshold and a second user-activated force threshold, compare the deflection signal to the first and second user-activated force thresholds, output a first signal when the deflection signal is less than the first user-activated force threshold, and output a second signal when the deflection signal is greater than the second user-activated force threshold.

The first user-activated force threshold and the second user-activated force threshold can be predetermined and stored within a memory of the controller. The controller can also include electrical circuitry that is configured to filter the received deflection signal so that unwanted frequencies can be attenuated. For example, the controller may apply a high-pass filter configured to remove above-threshold frequencies before evaluating the filtered signal to determine whether a tapping activity has occurred. Alternatively and/or additionally, the controller may apply a low-pass filter configured to remove below-threshold frequencies before evaluating the filtered signal to determine whether a puffing activity has occurred. The filtering of the deflection signal may increase the reliability of the controller detecting a tapping activity and/or a puffing activity including by eliminating noise that may be present in the deflection signal. As a result, the filtration can minimize false positives in detecting a user's puffing or tapping activity. Further, such filtration can help distinguish between a deflection signal associated with a puff and a deflection signal associated with a tap.

In instances, when the controller determines that a puff is occurring, the controller can prompt a power source (for example, a battery, which can be a rechargeable battery) to deliver electric current to a heating element (e.g., a resistive heater) of the vaporizer device. As a result, the heating element can be activated in association with a user puffing (e.g., drawing, inhaling, etc.) on the vaporizer device. As discussed in more detail below, once the heating element is activated, at least a portion of the vaporizable material in communication therewith can be vaporized.

Vaporizer devices for use with liquid vaporizable materials can include an atomizer. The atomizer can include a wicking element (i.e., a wick) configured to convey an amount of the vaporizable material to a part of the atomizer that includes a heating element.

For example, the wicking element can be configured to draw the vaporizable material from a reservoir configured to contain the vaporizable material, such that the vaporizable material can be vaporized by heat delivered from a heating element. The wicking element can also optionally allow air to enter the reservoir and replace the volume of vaporizable material removed. In some implementations of the current subject matter, capillary action can pull vaporizable material into the wick for vaporization by the heating element, and air can return to the reservoir through the wick to at least partially equalize pressure in the reservoir. Other methods of allowing air back into the reservoir to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer can include a heating element which includes a resistive coil or other heating element wrapped around, positioned within, integrated into a bulk shape of, pressed into thermal contact with, or otherwise arranged to deliver heat to a wicking element, to cause the vaporizable material drawn from the reservoir by the wicking element to be vaporized for subsequent inhalation by a user in a gas and/or a condensed (for example, aerosol particles or droplets) phase. Other wicking elements, heating elements, and/or atomizer assembly configurations are also possible.

After conversion of the vaporizable material to the gas phase, at least some of the vaporizable material in the gas phase can condense to form particulate matter in at least a partial local equilibrium with a portion of the vaporizable material that remains in the gas phase. The vaporizable material in the gas phase as well as the condensed phase are part of an aerosol, which can form some or all of an inhalable dose provided by the vaporizer device during a user's puff or draw on the vaporizer device. It should be appreciated that the interplay between the gas phase and condensed phase in an aerosol generated by a vaporizer device can be complex and dynamic, due to factors such as ambient temperature, relative humidity, chemistry, flow conditions in airflow paths (both inside the vaporizer device and in the airways of a human or other animal), and/or mixing of the vaporizable material in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

In instances, when the controller determines that a tap is occurring, for example, based on the deflection of the flexible sensor, the controller can also prompt the power source to deliver electric current to an output feature or device of the vaporizer device that provides information to the user. For example, in one embodiment, the output device can be a light source that, when actuated, represents a power condition of the power source at the time of the tapping. For example, in instances where the power source is a battery, the actuation of the light source can represent the real-time charge of the battery at the time of tapping. Alternatively or additionally, the actuation of the light source can provide feedback to a user based on a status and/or mode of operation of the vaporizer device at the time of tapping.

As discussed herein, the vaporizer device consistent with implementations of the current subject matter can be configured to connect (such as, for example, wirelessly or via a wired connection) to a computing device (or optionally two or more devices) in communication with the vaporizer device. To this end, the controller can include communication hardware. The controller can also include a memory. The communication hardware can include firmware and/or can be controlled by software for executing one or more cryptographic protocols for the communication.

A computing device can be a component of a vaporizer system that also includes the vaporizer device, and can include its own hardware for communication, which can establish a wireless communication channel with the communication hardware of the vaporizer device. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls.

In the example in which a computing device provides signals related to activation of the resistive heating element, or in other examples of coupling of a computing device with the vaporizer device for implementation of various control or other functions, the computing device executes one or more computer instruction sets to provide a user interface and underlying data handling. In one example, detection by the computing device of user interaction with one or more user interface elements can cause the computing device to signal the vaporizer device to activate the heating element to reach an operating temperature for creation of an inhalable dose of vapor/aerosol. Other functions of the vaporizer device can be controlled by interaction of a user with a user interface on a computing device in communication with the vaporizer device 100.

The temperature of a resistive heating element of the vaporizer device can depend on a number of factors, including an amount of electrical power delivered to the resistive heating element and/or a duty cycle at which the electrical power is delivered, conductive heat transfer to other parts of the electronic vaporizer device and/or to the environment, latent heat losses due to vaporization of the vaporizable material from the wicking element and/or the atomizer as a whole, and convective heat losses due to airflow (i.e., air moving across the heating element or the atomizer as a whole when a user inhales on the vaporizer device). As noted above, to reliably activate the heating element or heat the heating element to a desired temperature, a vaporizer device makes use of signals from a flexible sensor to determine when a user is inhaling.

To take measurements accurately and maintain durability of the vaporizer device, it can be beneficial to provide a seal resilient enough to separate an airflow path from other parts of the vaporizer device. The seal, which can be a gasket, can be configured to at least partially surround the flexible sensor such that connections of the flexible sensor to the internal circuitry of the vaporizer device are separated from a part of the flexible sensor exposed to the airflow path. In an example of a cartridge-based vaporizer device, the seal can also separate parts of one or more electrical connections between the vaporizer body and the vaporizer cartridge. Such arrangements of the seal in the vaporizer device can be helpful in mitigating against potentially disruptive impacts on vaporizer components resulting from interactions with environmental factors such as water in the vapor or liquid phases, other fluids such as the vaporizable material, etc., and/or to reduce the escape of air from the designated airflow path in the vaporizer device. Unwanted air, liquid or other fluid passing and/or contacting circuitry of the vaporizer device can cause various unwanted effects, such as altered pressure readings, and/or can result in the buildup of unwanted material, such as moisture, excess vaporizable material, etc., in parts of the vaporizer device where they can result in poor pressure signal, degradation of the flexible sensor or other components, and/or a shorter life of the vaporizer device. Leaks in the seal can also result in a user inhaling air that has passed over parts of the vaporizer device containing, or constructed of, materials that may not be desirable to be inhaled.

In some embodiments, the vaporizer device can include a cartridge that includes reservoir chamber that is configured to hold a vaporizable material. The cartridge can also include a second airflow path that extends therethrough and in fluid communication with the first airflow path. The cartridge can be selectively coupled to a vaporizer body, as discussed below. In some embodiments, the vaporizer body includes a cartridge receptacle that is configured to receive at least a portion of the cartridge.

In an embodiment of the vaporizer device in which the power source is part of the vaporizer body, and a heating element is disposed in the vaporizer cartridge and configured to couple with the vaporizer body, the vaporizer device can include electrical connection features (for example, means for completing a circuit) for completing a circuit that includes the controller (for example, a printed circuit board, a microcontroller, or the like), the power source, and the heating element (for example, a heating element within the atomizer). These features can include one or more contacts (referred to herein as cartridge contacts) on a bottom surface of the vaporizer cartridge and at least two contacts (referred to herein as receptacle contacts and) disposed near a base of the cartridge receptacle of the vaporizer device such that the cartridge contacts and the receptacle contacts make electrical connections when the vaporizer cartridge is inserted into and coupled with the cartridge receptacle. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts and the receptacle contacts can be configured to electrically connect in either of at least two orientations. In other words, one or more circuits necessary for operation of the vaporizer device can be completed by insertion of the vaporizer cartridge into the cartridge receptacle in a first rotational orientation (around an axis along which the vaporizer cartridge is inserted into the cartridge receptacle of the vaporizer body) such that a first cartridge contact is electrically connected to a first receptacle contact and a second cartridge contact is electrically connected to a second receptacle contact. Furthermore, the one or more circuits necessary for operation of the vaporizer device can be completed by insertion of the vaporizer cartridge in the cartridge receptacle in a second rotational orientation such the first cartridge contact is electrically connected to the second receptacle contact and the second cartridge contact is electrically connected to the first receptacle contact.

In one example of an attachment structure for coupling the vaporizer cartridge to the vaporizer body, the vaporizer body includes one or more detents (for example, dimples, protrusions, etc.) protruding inwardly from an inner surface of the cartridge receptacle, additional material (such as metal, plastic, etc.) formed to include a portion protruding into the cartridge receptacle, and/or the like. One or more exterior surfaces of the vaporizer cartridge can include corresponding recesses that can fit and/or otherwise snap over such detents or protruding portions when the vaporizer cartridge is inserted into the cartridge receptacle on the vaporizer body. When the vaporizer cartridge and the vaporizer body are coupled (e.g., by insertion of the vaporizer cartridge into the cartridge receptacle of the vaporizer body), the detents or protrusions of the vaporizer body can fit within and/or otherwise be held within the recesses of the vaporizer cartridge, to hold the vaporizer cartridge in place when assembled. Such an assembly can provide enough support to hold the vaporizer cartridge in place to ensure good contact between the cartridge contacts and the receptacle contacts, while allowing release of the vaporizer cartridge from the vaporizer body when a user pulls with reasonable force on the vaporizer cartridge to disengage the vaporizer cartridge from the cartridge receptacle.

In some implementations, the vaporizer cartridge, or at least an insertable end of the vaporizer cartridge configured for insertion in the cartridge receptacle, can have a non-circular cross section transverse to the axis along which the vaporizer cartridge is inserted into the cartridge receptacle. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts and the receptacle contacts can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge and the vaporizer body. The electrical contacts can optionally be gold-plated, and/or include other materials.

Further to the discussion above regarding the electrical connections between the vaporizer cartridge and the vaporizer body being reversible such that at least two rotational orientations of the vaporizer cartridge in the cartridge receptacle are possible, in some embodiments of the vaporizer device, the shape of the vaporizer cartridge, or at least a shape of the insertable end of the vaporizer cartridge that is configured for insertion into the cartridge receptacle, can have rotational symmetry of at least order two. In other words, the vaporizer cartridge or at least the insertable end of the vaporizer cartridge can be symmetrical upon a rotation of 180° around an axis along which the vaporizer cartridge is inserted into the cartridge receptacle. In such a configuration, the circuitry of the vaporizer device can support identical operation regardless of which symmetrical orientation of the vaporizer cartridge occurs.

FIG. 1 illustrates a schematic of an exemplary vaporizer device 100 that includes a vaporizer body 102, a vaporizer cartridge 104 that can be selectively coupled to and removable from the vaporizer body 102, and a sensor assembly 109 residing at least partially within the vaporizer body 102. The sensor assembly 109 can include a flexible sensor 106 configured to deflect in response to forces corresponding to, for example, a tapping activity, a puffing activity, and/or the like. For purposes of simplicity only, certain components of the vaporizer device 100 are not illustrated.

The vaporizer body 102 can have a variety of configurations. As shown in FIG. 1, the vaporizer body 102 includes a sleeve 108 that defines a cartridge receptacle 110 within the vaporizer body 102 that is configured to receive at least a portion of the vaporizer cartridge 104. Once the vaporizer cartridge 104 is coupled to the vaporizer body 102, a first airflow path 112 is created between a first wall 108a of the sleeve 108 that defines the cartridge receptacle 110 and an end surface 104a of the of the vaporizer cartridge 104. Further, as shown in FIG. 1, an air inlet 114 extends through a second wall 108b of the sleeve 108. This air inlet 114 is configured to allow at least a portion of ambient air outside of the vaporizer body 102 to be drawn into the vaporizer device 100 and along at least the first airflow path 112.

The vaporizer cartridge 104 includes a reservoir chamber 116 that is configured to hold a vaporizable material (not shown). While the reservoir chamber 116 can have a variety of sizes and shapes, the reservoir chamber 116, as shown in FIG. 1, is substantially rectangular in shape. In other embodiments, the reservoir chamber 116 can have any other possible shape.

Further, as shown in FIG. 1, the vaporizer cartridge 104 also includes an internal channel 118 that extends from an inlet 120 to an outlet 122 of the vaporizer cartridge 104. The internal channel 118 is configured to direct air and vaporized material through the vaporizer cartridge 104 and exit the outlet 122 for inhalation by a user. In use, a user can puff on an end 105 of the vaporizer cartridge 104 such that the air and vaporized material within the vaporizer cartridge 104 can be delivered directly to the user from the outlet 122 for inhalation. Alternatively, a mouthpiece (not shown) can be coupled to the end 105 of the vaporizer cartridge 104, in which case the user can puff on the mouthpiece rather than directly on the end 105 of the vaporizer cartridge 104. As such, the air and vaporized material within the vaporizer cartridge 104 can travel from the outlet 122 into the mouthpiece for inhalation by the user.

The vaporizer cartridge 104 also includes an atomizer 124. The atomizer 124 includes a heating element 125a and a wicking element 125b. The wicking element 125b is in fluid communication with the reservoir chamber 116 to draw vaporizable material (not shown) therefrom. As described in more detail below, once the heating element 125a is activated via a user puffing on the end 105 of the vaporizer cartridge 104, at least a portion of the vaporizable material within the wicking element 125b is vaporized into vaporized material. The vaporized material joins at least a portion of the air within the first airflow path 112 to form a mixture. The mixture travels through the remaining portion of the first airflow path 112 and then through a second airflow path 126 defined by the internal channel 118 of the vaporizer cartridge 104. As the mixture travels through at least the second airflow path 126, and thus, the internal channel 118 of the vaporizer cartridge 104, it at least partially condenses into aerosol for subsequent inhalation by a user.

Figure 2:
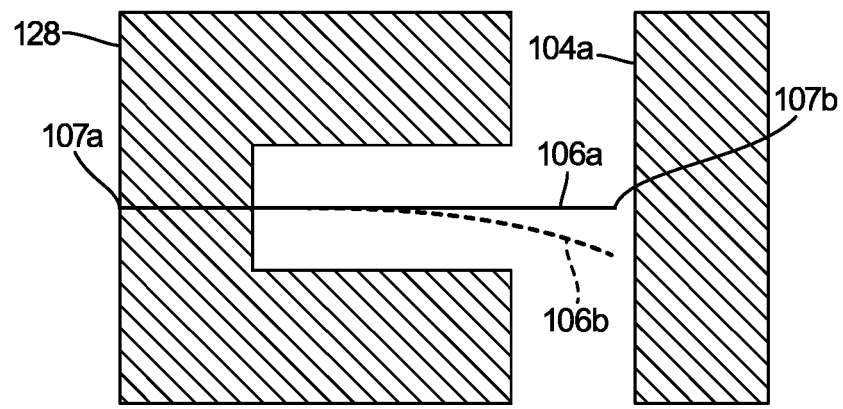
FIG. 2 is a magnified view of the flexible sensor in FIG. 1 when in an initial state (solid line) and in a deflected state (dashed line)

As shown in FIGS. 1-2, the flexible sensor 106 is in the form of a beam and extends from a first end 107a to a second end 107b. The first end 107a is fixedly attached to a substrate 128, whereas the second end 107b is positioned within the first airflow path 112. In this illustrated embodiment, the substrate 128 is coupled to a printed circuit board assembly 129. In other embodiments, the printed circuit board assembly 129 may be a part of the substrate 128.

The flexible sensor 106 is configured to reversibly deflect in response to a first user-activated force representing air being drawn through the first airflow path 112 (e.g., a puff activity) and in response to a second user-activated force representing acceleration of the vaporizer body 102 (e.g., a tap activity). Thus, by positioning the second end 107b within the first airflow path 112, a puffing activity or a tapping activity can cause the flexible sensor 106 to reversibly deflect from an initial state to a first state (e.g., during a puff on the device) or a second state (e.g., during a tap on the device), respectively. For illustration purposes only, FIG. 2 depicts an exemplary initial state of the flexible sensor 106 as a solid line 106a and an exemplary deflection state (e.g., a first state or a second state) as a dashed line 106b. In use, as a user puffs on the vaporizer device 100 (e.g., on the end 105 of the vaporizer cartridge 104 coupled to the vaporizer body 102) or taps on the vaporizer device 100 (e.g., on the vaporizer body 102, on the vaporizer cartridge 104 when coupled to the vaporizer body 102, or both), the flexible sensor 106 will deflect, thereby producing a deflection signal.

The flexible sensor 106 can be positioned anywhere along the first airflow path 112 that allows the flexible sensor 106 to reversibly deflect. However, in some embodiments, it may be desirable to position the flexible sensor 106 proximate to the air inlet 114, as shown in FIG. 1. In one embodiment, the flexible sensor 106 can be designed to and/or positioned within the first airflow path 112 such that the flexible sensor 106 can substantially seal the first airflow path 112 at least between puffing activities. This can increase puff detection sensitivity of the flexible sensor 106.

In some implementations of the current subject matter, the substrate 108 and/or the printed circuit board assembly 129 may include circuitry configured to respond to the a deflection of the flexible sensor 106 by generating a corresponding deflection signal. Moreover, with the substrate 108 and/or the printed circuit board assembly 129 may include circuitry configured to send, to the controller 130 residing within the vaporizer body 102, the deflection signal. The controller 130 is configured to receive and analyze the deflection signal to determine whether a puff or tap on the vaporizer device 100 has occurred. The controller 130 also includes a memory 132 that is configured to maintain a threshold frequency value associated with a puff activity (e.g., a first user-activated force threshold) and a threshold frequency value associated with a tapping activity (e.g., a first user-activated force threshold).

In use, the circuitry included in the substrate 108 and/or the printed circuit board assembly 129 may, upon detecting a deflection of the flexible sensor 106, send the corresponding deflection signal to the controller 130. The deflection signal is processed by the controller 130 and compared to threshold frequency values stored in the memory 132. In instances when the frequency value(s) associated with the deflection signal is less than the first frequency threshold, the controller 130 determines that a puff activity is occurring. As a result, the controller 130 sends a signal to a power source 134 residing within the vaporizer body 102 to cause the power source 134 to deliver elective current to the heating element 125a of the atomizer 124. Once the heating element 125a is activated at least a portion of vaporizable material within the wicking element 125b of the atomizer 124 is vaporized, and ultimately condensed and inhaled by the user, as discussed above. In contrast, when the frequency value(s) associated with the deflection signal is greater the second frequency threshold, the controller 130 determines that a tapping activity is occurring. As a result, the controller 130 sends a signal to the power source 134 to cause the power source 134 to deliver electric current to an output feature or device 136 (e.g., a light) within the vaporizer body 102 to indicate a real-time power condition of the power source 134.

Various techniques may be applied in order to increase the reliability of the controller 130 detecting a puffing activity and/or a tapping activity. For example, in some embodiments, the controller 130 may filter the deflection signal corresponding to the deflection of the flexible sensor 106. The controller 130 may apply a high-pass filter configured to remove above-threshold frequencies before evaluating the filtered signal to determine whether a tapping activity has occurred. Alternatively and/or additionally, the controller 130 may apply a low-pass filter configured to remove below-threshold frequencies before evaluating the filtered signal to determine whether a puffing activity has occurred. The filtering of the deflection signal may eliminate noise that may be present in the deflection signal, thereby increasing the reliability of the controller 130 detecting a tapping activity and/or a puffing activity.

Figure 3:
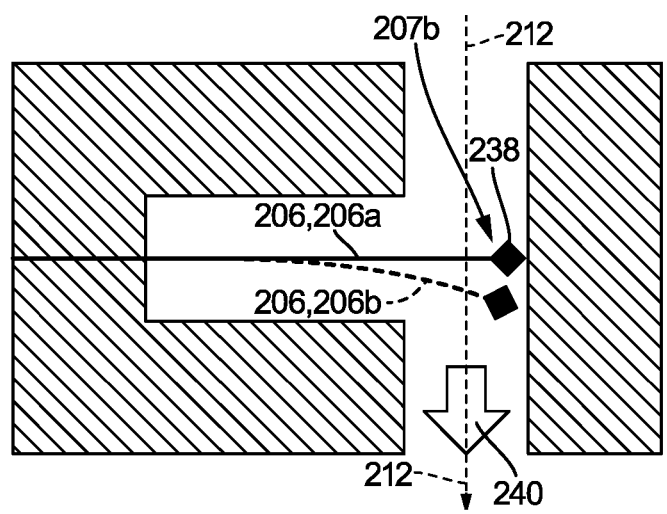
FIG. 3 is a schematic of a second embodiment of a flexible sensor when in an initial state (solid line) and in a deflected state (dashed line)

Alternatively and/or additionally, in some embodiments, the reliability of the controller 130 detecting a tapping activity and/or a puffing activity may be increased by mechanically amplifying the flexible sensor to at least enable the detection of small amplitude taps on the vaporizer device 100. For example, as shown in FIG. 3, a second end 207b of a flexible sensor 206 includes a weight element 238 coupled thereto. For illustration purposes only, FIG. 3 depicts an exemplary initial state of the flexible sensor 206 (e.g., prior to a puff or tap on the vaporizer device) as a solid line 206a and an exemplary deflection state (e.g., during a puff or a tap on the vaporizer device) of the flexible sensor 206 as a dashed line 206b with an arrow 240 depicting the direction of airflow along the first airflow path 212.

Figure 4:
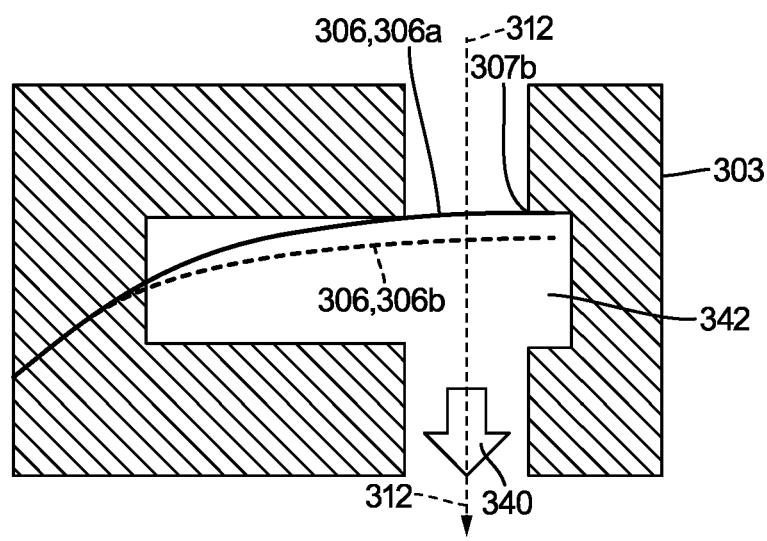
FIG. 4 is a schematic of a third embodiment of a flexible sensor when in an initial state (solid line) and in a deflected state (dashed line)

In other embodiments, the flexible sensor can be mechanically dampened, which may increase the reliability of the controller 130 detecting a tapping activity and/or a puffing activity by avoiding false negatives triggered by de minimis deflections of the flexible sensor. For example, as shown in FIG. 4, a flexible sensor 306 has a curved configuration in the initial state (e.g., prior to a puff or tap on the vaporizer device) such the flexible sensor 306 is preloaded. Further, in this illustrated embodiment, a cartridge wall 303 includes a cutout portion 342 such that a free end 307b of the flexible sensor 306 extends laterally across a first airflow path 312 so as to seal the first airflow path 312 between puffing and/or tapping on the vaporizer device. For illustration purposes only, FIG. 4 depicts an exemplary initial state of the flexible sensor 306 (e.g., prior to a puff or tap on the vaporizer device) as a solid line 306a and an exemplary deflection state (e.g., during a puff or a tap on the vaporizer device) of the flexible sensor 306 as a dashed line 306b with an arrow 340 depicting the direction of airflow through the first airflow path 312.

Figure 5:
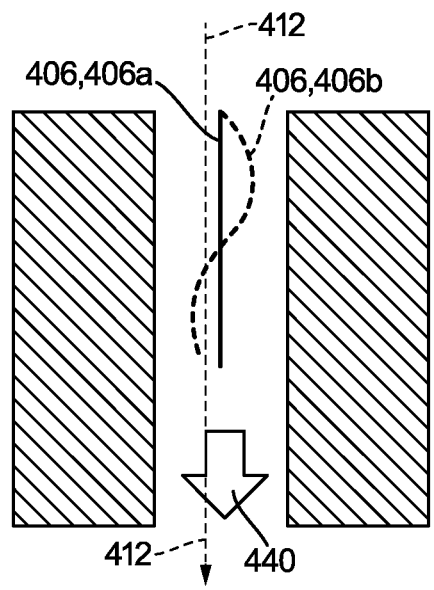
FIG. 5 is a schematic of a fourth embodiment of a flexible sensor when in an initial state (solid line) and in a deflected state (dashed line)

FIG. 5 illustrates another exemplary flexible sensor 406 in which the entire flexible sensor 406 resides with a first airflow path 412. As such, airflow passing along the first airflow path 412 causes the flexible sensor 406 to vibrate. As noted above, this effect is known as aerodynamic flutter. For illustration purposes only, FIG. 5 depicts an exemplary initial state of the flexible sensor 406 (e.g., prior to a puff or tap on the vaporizer device) as a solid line 406a and an exemplary deflection state (e.g., during a puff or a tap on the vaporizer device) of the flexible sensor 406 as a dashed line 406b with an arrow 440 depicting the direction of airflow through the first airflow path 412. In such embodiments, additional signal processing may be needed (e.g., filtering) to determine a puffing activity and/or a tapping activity. For example, additional signal processing can include bandpass filtering or a combination of low and/or high pass filtering, followed by examining the transient behavior of the generated signal of the flexible sensor 406 to determine if the signal spikes then decays quickly for a tapping activity, or remains high for a puffing activity.

Figure 6:
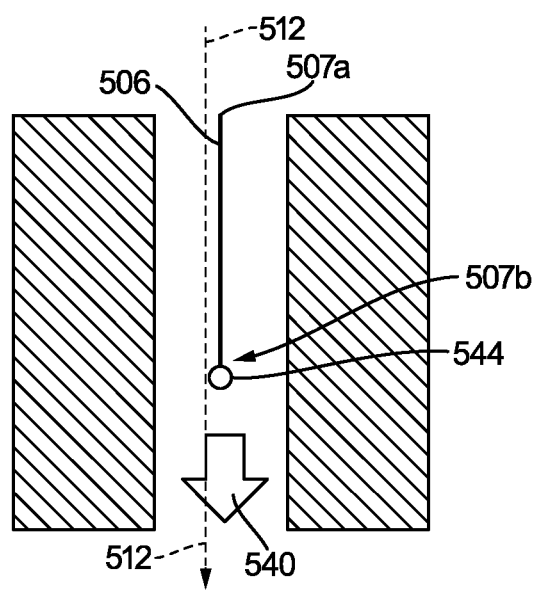
FIG. 6 is a schematic of a fifth embodiment of a flexible sensor.

In an effort to avoid the need for additional signal processing, the flexible sensor can include a bluff feature. For example, as shown in FIG. 6, a flexible sensor 506 extends from a first end 507a to a second end 507b, in which the second end 507b is downstream of the first end 507a within the first airflow path 512. The second end 507b includes a bluff feature 544 that is configured such that vortex shedding occurs as air passes along the flexible sensor 506 during a puffing activity. As a result, during a puffing activity, the air that passes in the direction of airflow 540, and thus through the first airflow path 512, causes alternating vortices to form at a certain frequency. This in turn produces a vibrational signal that can be detected, e.g., via a printed circuit board assembly coupled to the flexible sensor 506, and distinguished from a tapping activity by a controller, like controller 130 shown in FIG. 1, without the need for additional signal processing. During a tapping activity, the signal generated thereby includes a large impulse followed by a very short period of oscillation which rapidly decays. The bluff feature 544 can have a variety of configurations. For example, as shown in FIG. 6, the bluff feature 544 is spherical in shape, whereas in other embodiments, the bluff feature 544 can have any other suitable shape, e.g., a rectangular shape.

Figure 7:
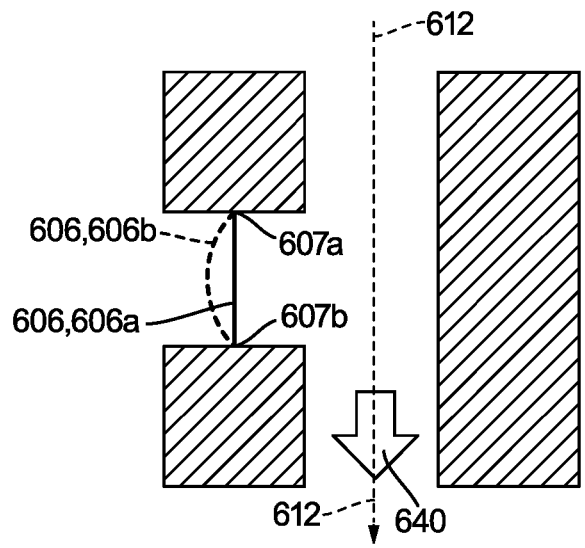
FIG. 7 is a schematic of a sixth embodiment of a flexible sensor when in an initial state (solid line) and in a deflected state (dashed line)

FIG. 7 illustrates another exemplary flexible sensor 606. As shown, each end 607a, 607b of the flexible sensor 606 is fixedly attached to first and second substrates such that the flexible sensor 606 defines a portion of a first airflow path 612. As a result, the flexible sensor 606 can reversibly bend in response to a puff or tap on the device. For illustration purposes only, FIG. 7 depicts an exemplary initial state of the flexible sensor 606 (e.g., prior to a puff or tap on the vaporizer device) as a solid line 606a and an exemplary deflection state (e.g., during a puff or a tap on the vaporizer device) of the flexible sensor 606 as a dashed line 606b with an arrow 640 depicting the direction of airflow through the first airflow path 612.

Figure 8:
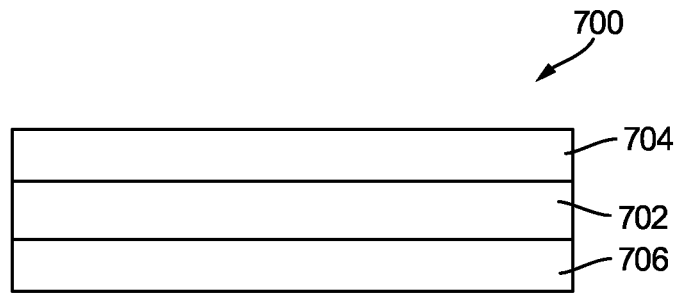
FIG. 8 is a schematic of a seventh embodiment of a flexible sensor.

In some implementations of the current subject matter, the deflection of the flexible sensor may be detected based on an electric current generated by the flexible sensor. For example, any of the flexible sensors described herein, such as those illustrated in FIGS. 1-7, can be in the form of a piezoelectric film. In one exemplary embodiment, as illustrated in FIG. 8, a piezoelectric film 700 can be a three-layered laminate that includes a piezoelectric layer 702 of piezoelectric material(s) interposed between two conductive layers 704, 706. The piezoelectric layer 702 can be formed of one or more piezoelectric materials. Non-limiting examples of suitable piezoelectric materials include polyvinylidene fluoride (PVDF) and the like. The two conductive layers 704, 706 can each be formed of one or more conductive materials. Non-limiting examples of one or more conductive materials include conductive inks infused with silver, graphite, and/or other conductive metals, conductive metal flakes or powders, and the like. In some embodiments, each of the two conductive layers 704, 706 can be formed of the same one or more conductive materials relative to one another, whereas in other embodiments, each of the two conductive layers 704, 706 can each be formed of different one or more conductive materials relative to one another.

Figure 9:
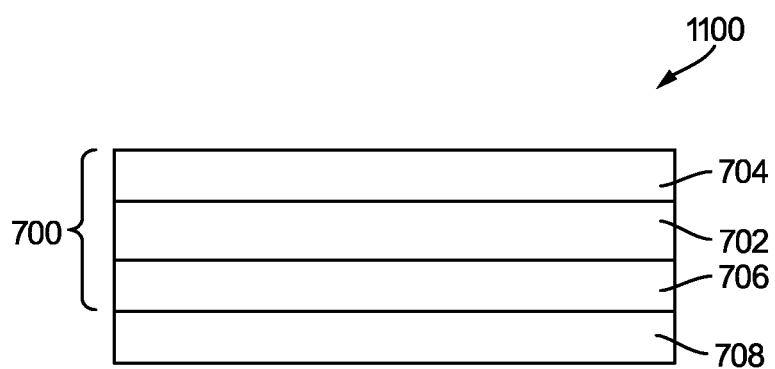
FIG. 9 is a schematic of an eighth embodiment of a flexible sensor.

In some implementations of the current subject matter, a piezoelectric film can be laminated to a substrate, for example, as shown in FIG. 9, in which piezoelectric film 700 is laminated to substrate 708, thereby forming flexible sensor 1100. In this way, the piezoelectric film 700 is positioned off the neutral axis of the flexible sensor 1100. As a result, upon deflection of the flexible sensor 1100 during a puffing activity and/or tapping activity, a net strain is produced, and therefore, a larger current is generated compared to instances where the piezoelectric film 700 is not laminated to a substrate, for example, as shown in FIG. 8. The substrate can be formed of any suitable material. Non-limiting examples of suitable substrate materials include one or more polymers, such as polyethylene terephthalate.

The piezoelectric layer 702 may be configured to generate, in response to the deflection of the flexible sensor, an electric current that is conveyed to a printed circuit board assembly coupled with the flexible sensor by the conductive layer 704 and/or the conductive layer 706. The printed circuit board assembly may include circuitry configured to generate, based on one or more characteristics of the electric current, a corresponding deflection signal indicative of whether a tapping activity or a puffing activity has occurred at the vaporizer device, like vaporizer device 100 shown in FIG. 1. For example, the printed circuit board assembly may include circuitry configured to determine, based on an amplitude and/or frequency of the electric current, whether a tapping activity or a puffing activity has occurred at the vaporizer device, like vaporizer device shown in FIG. 1.

Figure 10:
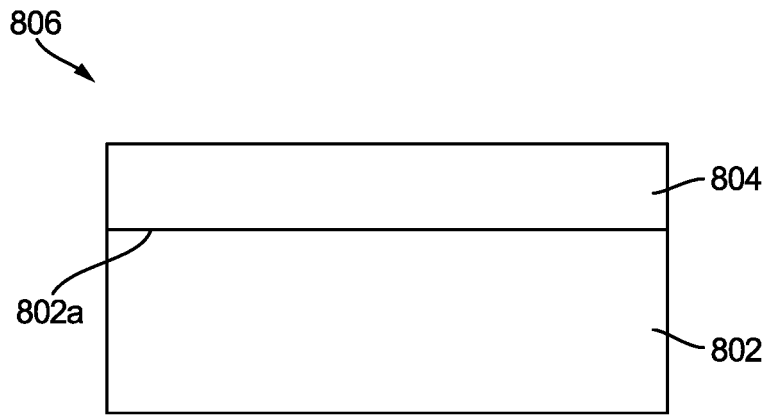
FIG. 10 is a schematic of a ninth embodiment of a flexible sensor.

In another exemplary embodiment, a flexible sensor can include at least one conductive polymer. For example, as shown in FIG. 10, the flexible sensor 806 can include a base layer 802 and a conductive layer 804 that is printed on a surface 802a of the base layer 802. The base layer 802 can be formed of one or more polymers or elastomers loaded with conductive material such as graphite, carbon, metal flakes or powders, and/or any combination thereof. The conductive layer 804 can be formed of a polymer containing conductive particles that are configured to move apart when the flexible sensor deflects (e.g., bends in one direction) in response to a puffing or taping activity. Non-limiting examples of suitable conductive particles include carbon, graphite, and metal particles. Deflection of the flexible sensor, which changes the organization of the conductive particles, may change the conductivity of the flexible sensor

806. Accordingly, a printed circuit board assembly coupled with the flexible sensor 806 may include circuitry that is configured to detect a deflection of the flexible sensor 806 based on a conductivity profile of the flexible sensor 806, which may include, for example, a change in the conductivity of the flexible sensor 806, a rate of change in the conductivity of the flexible sensor 806, and/or the like. Alternatively and/or additionally, the circuitry may be configured to detect the occurrence of a tapping activity or a puffing activity based on the conductivity profile of the flexible sensor 806.

Figure 11A:
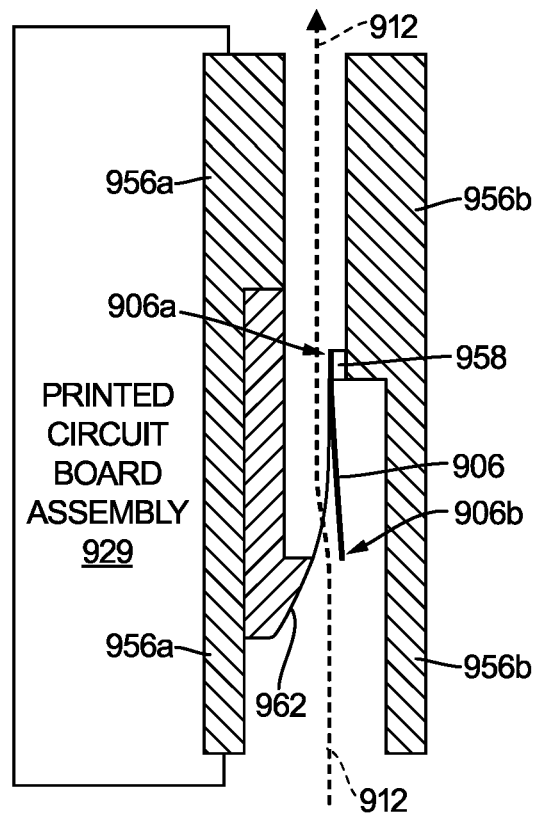
FIG. 11A is a schematic of a tenth embodiment of a flexible sensor when in an initial state.
Figure 11B:
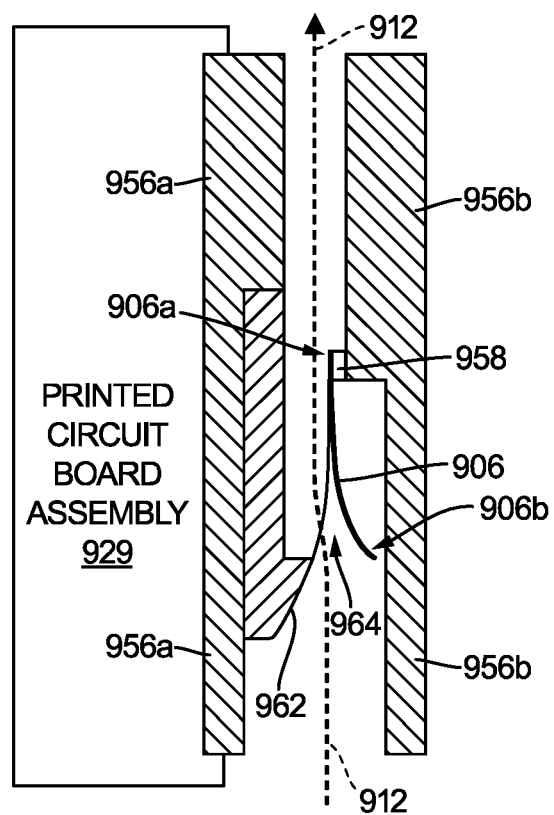
FIG. 11B is the flexible sensor in FIG. 11A when in a deflected state.

FIGS. 11A-11B illustrates another exemplary flexible sensor 906 that extends through a first airflow path 912. The first airflow path 912 is defined by a first substrate 956a and a second, opposing substrate 956b. As such, the structural dimensions of the first airflow path 912 (e.g., length and width) depends at least in part upon the structural configurations of each of the first and second substrates 956a, 956b. In this illustrated embodiment, the flexible sensor 906 extends from a first end 906a to a second, opposing end 906b. As shown, the first end 906a is coupled to a support 958 and the second end 906b is a free end so that the flexible sensor 906 can deflect in response to puffing and tapping activities. The support 958 is coupled to and extends from the second substrate 956b and into the first airflow path 912. As such, the entire flexible sensor 906 resides within the first airflow path 912. Further, a sounding board element is coupled to and extends along a portion of the first substrate 956a such that at least a portion of an edge 962 of the sounding board element extends parallel to a portion of the flexible sensor 906 when the flexible sensor 906 is an exemplary initial state (e.g., prior to a puff or tap on the vaporizer device), as shown in FIG. 11A. In other embodiments, the sounding board element can be formed as part of the first substrate 956a.

In use, during a puffing activity, as air flows through the first airflow path 912, at least a portion of the flexible sensor 906 deflects away from the edge 962 of the sounding board element thereby creating a wider gap 964 therebetween, as shown in FIG. 11B, which in turn produces a standing wave having a first frequency. Thus, the first frequency depends at least in part on the length of the first airflow path 912 and the space of the gap 964. This first frequency can then be detected and sent by the printed circuit board assembly 929 to a controller, like controller 130 shown in FIG. 1, such that the controller can communicate with a power source, like power source 134, as discussed above. Further, when a tapping activity occurs, the flexible sensor 906 deflects at a second, different frequency that is different than the first frequency. This second frequency can then be detected and sent by the printed circuit board assembly 929 to the controller, such that the controller can communicate with the power source, as discussed above.

Figure 12:
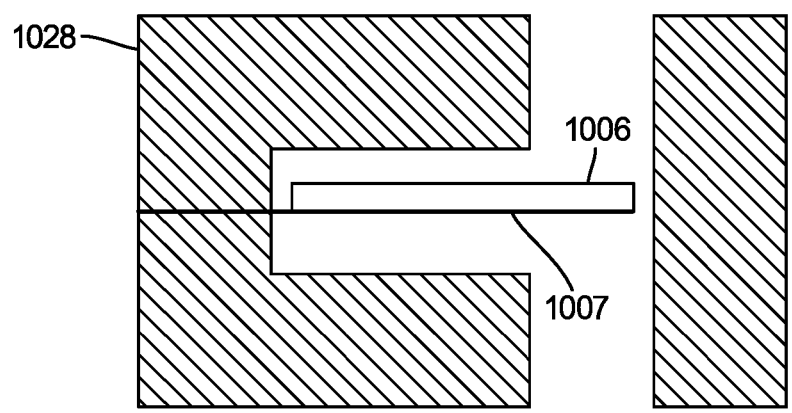
FIG. 12 is a schematic of an eleventh embodiment of a flexible sensor.

FIG. 12 illustrates another exemplary flexible sensor 1006 that is in the form of a strain gauge that is coupled to a portion of a beam 1007 that is coupled to a substrate 1028. While not shown in detail, the illustrated strain gauge includes a metallic trace coupled to an insulating flexible substrate, away from a principle axis, that is coupled to the beam 1007. As such, during puffing and/or tapping on the vaporizer device, the strain gauge can be stretched, thereby deforming the trace causing the electrical resistance to change. A printed circuit board assembly (e.g., like printed circuit board assembly 129 shown in FIG. 1) may include circuitry configured to detect the resistance profile of the strain gauge and send, to a controller (e.g., the controller 130 shown in FIG. 1) one or more corresponding signals. For example, the printed circuit board assembly may be configured to generate the one or more signals based on the resistance across the strain gauge, a change in the resistance across the strain gauge, a frequency of the change in the resistance across the strain gauge, and/or the like. Moreover, as discussed above, the controller can control, based at least on these signals, the operations of a power source, like power source 134.

TERMINOLOGY

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together."

A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the exemplary embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A vaporizer device, comprising:
   a vaporizer body including a first airflow path extending at least partially therethrough; and
   a sensor assembly residing at least partially within the vaporizer body, the sensor assembly including:
   a flexible sensor that is in communication with the first airflow path, the flexible sensor being adapted to reversibly deflect from an initial state to a first state in response to a first user-activated force representing air being drawn through the first airflow path, and the flexible sensor being adapted to reversibly deflect from the initial state to a second state in response to a second user-activated force representing an acceleration of the vaporizer body, wherein the first user-activated force and the second user-activated force are detected by a mechanical response of the flexible sensor.

2. The vaporizer device of claim 1, wherein the acceleration occurs in response to a user tapping the vaporizer body.

3. The vaporizer device of claim 1, wherein the flexible sensor at least partially resides within the first airflow path.

4. The vaporizer device of claim 1, wherein the sensor assembly includes a substrate residing within the vaporizer body, and wherein a first end of the flexible sensor is coupled to the substrate and a second, opposing end of the flexible sensor is positioned in the first airflow path.

5. The vaporizer device of claim 4, wherein the substrate includes a printed circuit board assembly.

6. The vaporizer device of claim 4, wherein the substrate is coupled to a printed circuit board assembly that at least partially resides within the vaporizer body.

7. The vaporizer device of claim 1, wherein the sensor assembly includes a first substrate and a second substrate that each reside within the vaporizer body, wherein a first end of the flexible sensor is coupled to the first substrate and a second, opposing end of the flexible sensor is coupled to the second substrate such that the flexible sensor defines a portion of the first airflow path.

8. The vaporizer device of claim 1, wherein the flexible sensor is configured to at least partially deflect at a first rate of deflection while the first user-activated force is being applied.

9. The vaporizer device of claim 8, wherein the flexible sensor is configured to at least partially deflect at a second rate of deflection while the second-user activated force is being applied.

10. The vaporizer device of claim 1, wherein the flexible sensor deflects at a first frequency while the flexible sensor is in the first state, and wherein the flexible sensor deflects at a second frequency that is different than the first frequency while the flexible sensor is in the second state.

11. The vaporizer device of claim 1, further comprising a weight element that is coupled to an end of the flexible sensor that resides within a portion of the first airflow path.

12. The vaporizer device of claim 1, wherein the flexible sensor in the initial state is straight.

13. The vaporizer device of claim 1, wherein the flexible sensor in the initial state is curved.

14. The vaporizer device of claim 1, wherein the flexible sensor is configured as a cantilever.

15. The vaporizer device of claim 1, wherein the flexible sensor comprises a strain gauge.

16. The vaporizer device of claim 1, wherein the flexible sensor is formed of at least one conductive polymer and/or at least one piezoelectric material.

17. The vaporizer device of claim 1, further comprising a controller configured to:
   receive a deflection signal in response to deflection of the flexible sensor;
   maintain a first user-activated force threshold and a second user-activated force threshold;
   compare the deflection signal to the first and second user-activated force thresholds;
   output a first signal when the deflection signal is less than the first user-activated force threshold; and
   output a second signal when the deflection signal is greater than the second user-activated force threshold.

18. The vaporizer device of claim 17, wherein the deflection of the flexible sensor is from the initial state to the first state or from the initial state to the second state.

19. The vaporizer device of claim 17, further comprising a heating element, wherein the output of the first signal is operable to cause an activation of the heating element to vaporize at least a portion of vaporizable material within a reservoir of the vaporizer device.

20. The vaporizer device of claim 17, further comprising a light source, wherein the vaporizer body includes a power source, and wherein the output of the second signal is operable to cause activation of the light source representing a power condition of the power source.

* * * * *